United States Patent
Govari et al.

(10) Patent No.: US 9,554,847 B2
(45) Date of Patent: Jan. 31, 2017

(54) REAL TIME ASSESSMENT OF ABLATION FROM ELECTROCARDIOGRAM SIGNALS

(75) Inventors: Assaf Govari, Haifa (IL); Athanassios Papaioannou, Los Angeles, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 415 days.

(21) Appl. No.: 13/539,628

(22) Filed: Jul. 2, 2012

(65) Prior Publication Data

US 2014/0005664 A1  Jan. 2, 2014

(51) Int. Cl.
*A61B 18/14* (2006.01)
*A61B 18/00* (2006.01)

(52) U.S. Cl.
CPC .. *A61B 18/1492* (2013.01); *A61B 2018/00357* (2013.01); *A61B 2018/00577* (2013.01); *A61B 2018/00708* (2013.01); *A61B 2018/00839* (2013.01)

(58) Field of Classification Search
None
See application file for complete search history.

(56) References Cited

U.S. PATENT DOCUMENTS

| | | | |
|---|---|---|---|
| 4,892,102 A * | 1/1990 | Astrinsky | 600/374 |
| 5,579,764 A | 12/1996 | Goldreyer | |
| 5,738,105 A * | 4/1998 | Kroll | 600/510 |
| 6,405,067 B1 * | 6/2002 | Mest et al. | 600/374 |
| 6,408,199 B1 * | 6/2002 | Goldin | 600/374 |
| 6,912,418 B1 * | 6/2005 | Florio | 607/9 |
| 6,922,579 B2 * | 7/2005 | Taimisto et al. | 600/374 |
| 7,419,487 B2 * | 9/2008 | Johnson et al. | 606/41 |
| 7,567,835 B2 * | 7/2009 | Gunderson et al. | 600/509 |
| 7,959,630 B2 | 6/2011 | Taimisto et al. | |
| 8,540,710 B2 * | 9/2013 | Johnson et al. | 606/41 |
| 2006/0253115 A1 | 11/2006 | Avitall et al. | |
| 2007/0006254 A1 | 1/2007 | Yun | |
| 2007/0062547 A1 | 3/2007 | Pappone | |
| 2008/0281314 A1 * | 11/2008 | Johnson et al. | 606/34 |
| 2010/0331658 A1 | 12/2010 | Kim et al. | |
| 2011/0098761 A1 | 4/2011 | Wittenberger | |
| 2011/0152854 A1 | 6/2011 | Beeckler et al. | |
| 2012/0035601 A1 * | 2/2012 | Wittenberger | 606/21 |

OTHER PUBLICATIONS

European Search Report, Application No. 13174359.3-1659, dated Nov. 6, 2013, 8 pages.

* cited by examiner

*Primary Examiner* — Brian T Gedeon
(74) *Attorney, Agent, or Firm* — Wayne C. Jaeschke, Jr.

(57) ABSTRACT

An apparatus includes an intra-body probe and a processor. The intra-body probe includes an electrode, which is configured to contact tissue in a heart. The processor is configured to receive an electrical signal from the electrode, to distinguish a local component, due to the tissue with which the electrode is in contact, in the electrical signal from a remote-field contribution to the signal, and to control a therapeutic procedure applied to the tissue responsively to the distinguished local component.

15 Claims, 3 Drawing Sheets

REAL TIME ASSESSMENT OF ABLATION FROM ELECTROCARDIOGRAM SIGNALS

FIELD OF THE INVENTION

The present invention relates generally to cardiac therapy, and particularly to methods and systems for monitoring cardiac signals during ablation therapy.

BACKGROUND OF THE INVENTION

Various techniques are known in the art for cardiac ablation therapy. U.S. Patent Publication No. 2010/0331658, whose disclosure is incorporated herein by reference, describes an open-irrigated catheter system comprising a tip section, a distal insert, and mapping electrodes. The tip section has an exterior wall that defines an open interior region within the tip section. The exterior wall includes mapping electrode openings and irrigation ports. The exterior wall is conductive for delivering radio frequency (RF) energy for an RF ablation procedure. The irrigation ports are in fluid communication with the open interior region to allow fluid to flow from the open interior region through the irrigation ports. The distal insert is positioned within the tip section to separate the open region into a distal fluid reservoir and a proximal fluid reservoir. The mapping electrodes are positioned in the mapping electrode openings in the tip section.

U.S. Patent Publication No. 2007/0006254, whose disclosure is incorporated herein by reference, describes a method of controlling a remote navigation system that orients the distal end of a medical device in response to user inputs, including interrupting the operation of the remote navigation system when the user inputs would navigate the medical device to a location where the impedance exceeds a predetermined value. A method of controlling ablation of cardiac tissue to block an errant signal causing an arrhythmia includes ablating tissue until there is a predetermined reduction in the amplitude of the errant signal or a predetermined reduction in local impedance.

U.S. Pat. No. 7,959,630, whose disclosure is incorporated herein by reference, describes assemblies, probes, and methods for creating circumferential lesions in tissue, e.g., the tissue within or around the ostium of a vessel. An ablation probe with an ablative structure can be placed in contact within or around the ostium of the vessel. A diagnostic probe can be introduced through a lumen within the ablation probe and inserted into the vessel. Energy can be provided to the ablative structure to create a circumferential lesion within or around the ostium of the vessel, and the diagnostic structure can be used to diagnose the tissue to determine whether the circumferential lesion can be properly created.

U.S. Patent Publication No. 2006/0253115, whose disclosure is incorporated herein by reference, describes catheters, systems, and methods which are provided for performing medical procedures, such as tissue ablation, adjacent the ostia of anatomical vessels, such as pulmonary veins. A catheter comprises an elongated flexible catheter body including a proximal shaft portion and a distal shaft portion, which has a proximal section pre-shaped to form a curve having an apex sized to be inserted into an anatomical vessel, such as a pulmonary vein, and a distal section configured to contact an ostium of the vessel when the curve apex is inserted within the vessel ostium. The catheter further comprises a steering mechanism configured for decreasing a radius of curvature of the curve.

SUMMARY OF THE INVENTION

An embodiment of the present invention provides an apparatus including an intra-body probe and a processor. The intra-body probe includes an electrode, which is configured to contact tissue in a heart. The processor is configured to receive an electrical signal from the electrode, to distinguish a local component, due to the tissue with which the electrode is in contact, in the electrical signal from a remote-field contribution to the signal, and to control a therapeutic procedure applied to the tissue responsively to the distinguished local component.

In some embodiments, the therapeutic procedure includes cardiac ablation therapy. In other embodiments, the intra-body probe includes an additional electrode that is configured to apply an ablation signal to the heart tissue. In other embodiments, the electrode applies an ablation signal to the tissue in the heart. Yet in other embodiments, the signal includes a received electrocardiogram (ECG) signal. In some embodiments, the local component is in response to cardiac electrical activity generated in the heart within a target ablation region, and the remote-field contribution is in response to cardiac electrical activity generated in the heart outside the target ablation region.

In some embodiments, the processor is configured to distinguish the local component by identifying one or more time intervals in the received signal in response to a change therein. In other embodiments, the processor is configured to distinguish the remote-field contribution by detecting no change in the received signal in one or more additional time intervals outside of the one or more identified time intervals. In yet other embodiments, the processor is configured to initiate a termination of an ablation procedure by detecting that the signal within the one or more identified time intervals no longer responds to successive ablation cycles.

There is also provided, in accordance with embodiments of the present invention, a method including receiving an electrical signal from an intra-body probe, which includes an electrode configured to contact tissue in a heart. A local component, due to the tissue with which the electrode is in contact, in the electrical signal is distinguished from a remote-field contribution to the signal. A therapeutic procedure applied to the tissue is controlled responsively to the distinguished local component.

The present invention will be more fully understood from the following detailed description of the embodiments thereof, taken together with the drawings in which:

DETAILED DESCRIPTION OF EMBODIMENTS

Overview

Ablation is a known technique for the treatment of various cardiac conditions. In an ablation procedure, an intra-body probe, typically a catheter, is percutaneously inserted into the cardiovascular system of a patient and navigated into the heart to a region of tissue to be ablated. Cardiac ablation can be performed with different modalities, such as cryoablation and radio frequency (RF) ablation therapies wherein the distal tip of the catheter can respectively be used to locally freeze or heat the tissue. In both cases, a lesion with a low conductance is formed. The lesion typically blocks the faulty pathways of the heart's electrical signals causing cardiac dysfunction, such as tachyarrhythmias and atrial fibrillation.

Real time monitoring of electrocardiogram (ECG) signals while performing the ablation therapy is beneficial for assessing the lesion, e.g., to check if the procedure has improved the heart function, or if more ablation needs to be delivered to the patient. Such real time monitoring may prevent terminating the procedure prematurely. However, if too much ablation is applied to the heart tissue, irreparable damage to the heart may result.

Embodiments of the present invention that are described herein provide methods and systems for a real time assessment of electrical signals received by an intra-body probe contacting heart tissue during a therapeutic procedure, such as cardiac ablation, so as to control the procedure in response to monitoring the signals. The intra-body probe, typically a catheter comprising an electrode, is navigated into the heart cavity to a target ablation region and receives a cardiac electrical signal from the electrode contacting the target ablation region.

A monitoring system is configured to distinguish, in a received electrical signal a remote-field contribution from a local component of the signal. The signal is typically an electrocardiogram (ECG) signal. The local component is due to the electrical activity at the target ablation region, whereas the remote-field contribution is due to electrical activity outside the target region. The system then controls the therapeutic procedure in response to the distinguished local component by invoking actions, such as by causing the ablation system to automatically terminate the ablation procedure, or by notifying an operator of the system on a monitor of the status of the ablation procedure. Such notification may avoid damage to the heart by over-ablation.

System Description

Figure 1:
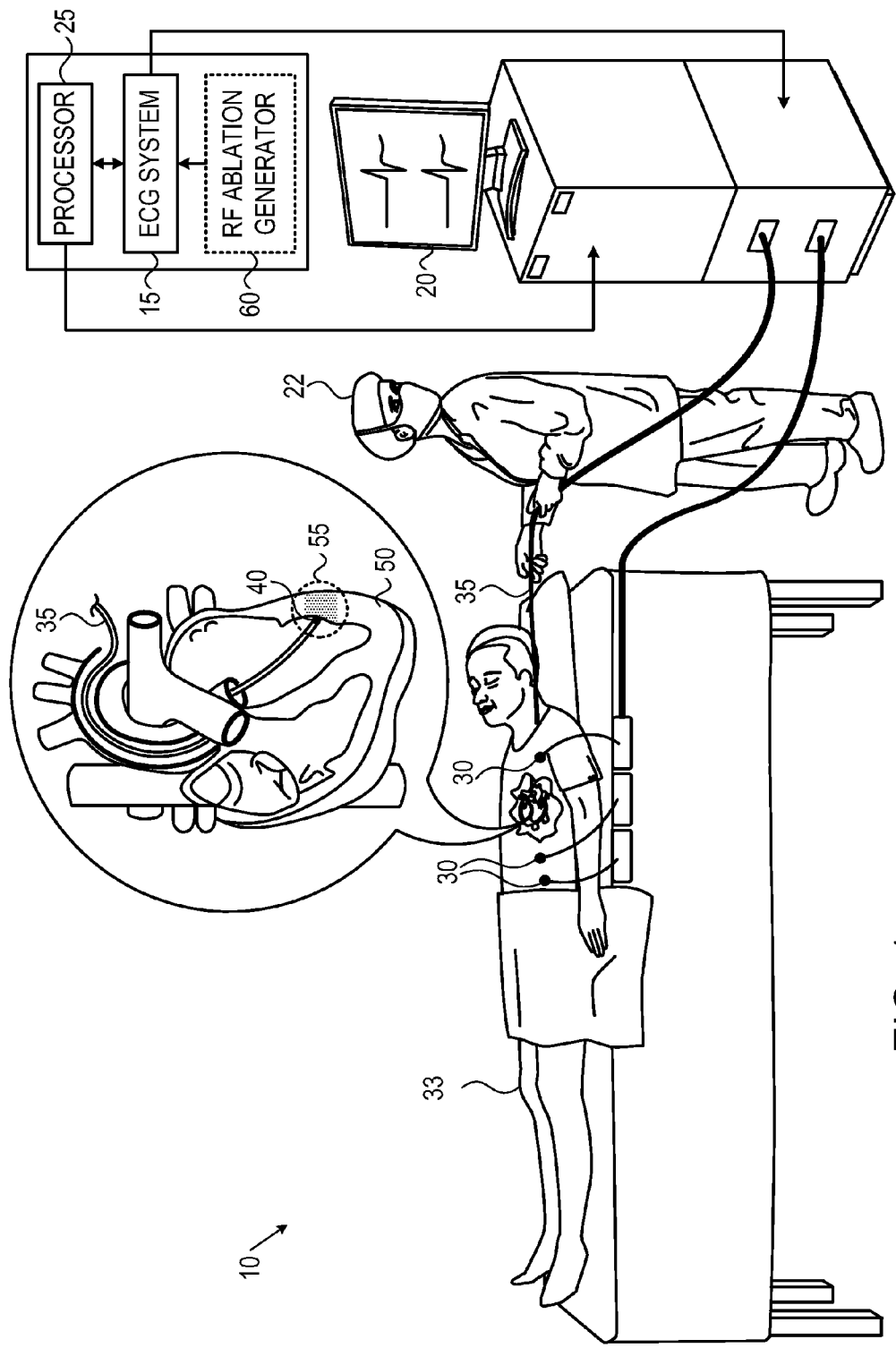
FIG. 1 is a schematic diagram showing an electrocardiogram ablation monitoring system, in accordance with an embodiment of the present invention.

FIG. 1 is a schematic diagram showing an electrocardiogram ablation monitoring system 10, in accordance with an embodiment of the present invention. System 10 comprises an ECG system 15, a display monitor 20 for an operator 22 to observe the ECG signal status, and a processor 25 for monitoring the received ECG data. In some embodiments, the system may also comprise ECG body electrodes 30 which may be placed at different positions along a body of a patient 33 and also utilized in monitoring ECG signals.

During a heart ablation procedure, an intra-body probe, typically a catheter 35 comprising an electrode 40 formed at the distal tip, is inserted into patient 33. Catheter 35 is navigated through the patient's cardiovascular system and into a heart 50 to contact a target ablation region 55 in the heart tissue. Electrode 40 of catheter 35 is utilized by ECG system 15 to measure an ECG signal.

In some embodiments, ablation may be applied to region 55 through a separate catheter, or any other appropriate therapeutic procedure, and the ECG signal monitored through catheter 35. In other embodiments utilizing radio frequency (RF) ablation therapy, the electrode at the distal tip of catheter 35 may be used to both receive the ECG signal at region 55 and also apply an RF ablation signal to region 55 from an RF ablation generator 60, as shown in the inset block diagram of FIG. 1. In yet other embodiments, catheter 35 may comprise an RF ablation electrode at the distal tip and a separate electrode formed on the body of catheter 35 typically near the distal tip.

Positioning electrode 40 to be in contact with ablation region 55 enables the electrode to receive an ECG signal from the region. As is explained in more detail below, the ECG signal comprises a local component due to cardiac electrical activity generated within target ablation region 55, superimposed with remote-field cardiac electrical potentials generated in heart 50 at positions outside target ablation region 55. The blood, for example, can form a conductive path for electrical cardiac activity occurring in any region of the heart outside of target ablation region 55, and relay the activity to catheter electrode 40 contacting the heart tissue in region 55, resulting in a remote-field contribution of the received ECG waveform.

Typically, faulty electrical pathways in region 55 of the heart causing cardiac dysfunction as discussed previously are incrementally removed with successive ablation cycles. As a result, one or more time intervals in which the ECG waveform decreases in amplitude, or changes shape, can be identified as the local component of the electrical cardiac activity detected from region 55, which is responding to the therapeutic cardiac ablation therapy. Processor 25 is configured to identify and track changes in the ECG waveform with the application of successive ablation cycles to the patient. The embodiment of the present invention shown in FIG. 1 is for conceptual clarity and not by way of limitation of the present invention.

Processor 25 typically comprises a general-purpose computer, with suitable front end and interface circuits for receiving ECG waveform data from ECG system 15 from catheter electrode 40 and body electrodes 30 contacting patient 33. The processor may also comprise magnetic, optical, electronic or any appropriate data storage device for storing the received ECG waveform data. The processor may be programmed in software to carry out the functions that are described herein. The software may be downloaded to system 10 in electronic form, over a network, for example, or it may be provided on non-transitory tangible media, such as optical, magnetic or electronic memory media. Alternatively, some or all of the functions of processor 25 may be carried out by dedicated or programmable digital hardware components. Based on signals received from the catheter electrode and body electrodes, processor 25 drives display monitor 20 to provide operator 22 with a visual display of the change of the ECG signal in the defined time intervals with successive ablation cycles. Display monitor 20 may also provide status information and guidance regarding the procedure that is in progress.

Figure 2:
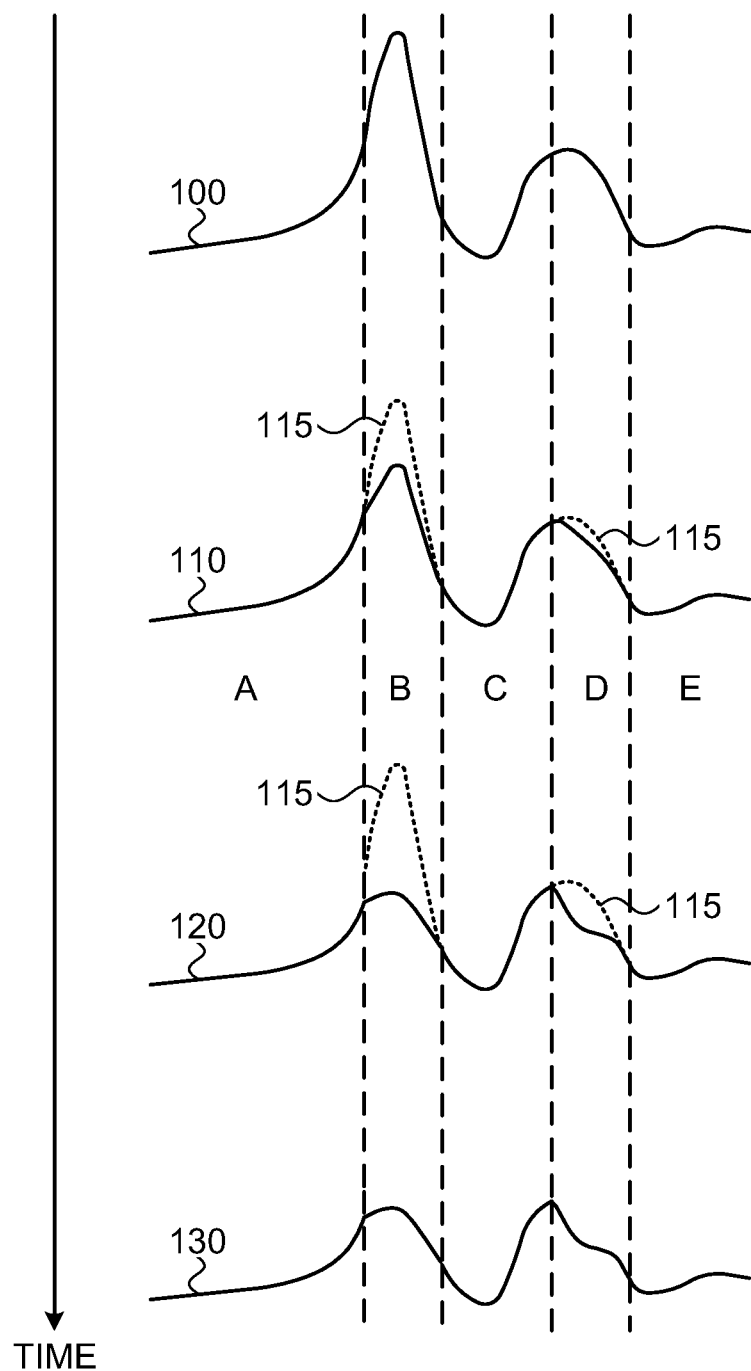
FIG. 2 is a schematic diagram showing changes in the ECG waveform with successive ablation cycles, in accordance with an embodiment of the present invention.

FIG. 2 is a schematic diagram showing changes in the ECG waveform with successive ablation cycles, in accordance with an embodiment of the present invention. Before the application of ablation therapy, an initial ECG waveform 100 is detected by ECG system 15. After an ablation cycle is applied, a first subsequent ECG waveform 110 changes in response to the ablation relative to initial waveform 100. Processor 25 identifies one or more time intervals of the ECG waveform, such as regions B and D as shown in FIG. 2 where the ECG signal decreases. Processor 25 identifies one or more additional time intervals of the ECG waveform, such as regions A, C, and E where the ECG signal remains unchanged. Regions B and D are assumed to be related to the local component of the received ECG signal and regions A, C, and E are assumed to be related to the remote-field contribution to the ECG signal from electrical cardiac events outside target ablation region 55.

With another ablation cycle as shown in a second subsequent waveform 120, the signal of the ECG waveform in regions B and D continues to decrease as the ablation decreases the local conductivity of the ablated heart tissue. Note that initial ECG waveform 100 prior to ablation is shown as a dotted line 115 on waveforms 110,120 merely for reference and conceptual clarity. Ablation therapy is continued until the system identifies no further changes in the ECG waveform (e.g., in regions B and D) with successive ablation cycles, as shown as a final ECG waveform 130. At this stage, system 10 is configured to terminate the ablation therapy, or to notify operator 22 that the ECG waveform no longer responds to ablation as described previously, so as not to damage the heart tissue.

Figure 3:
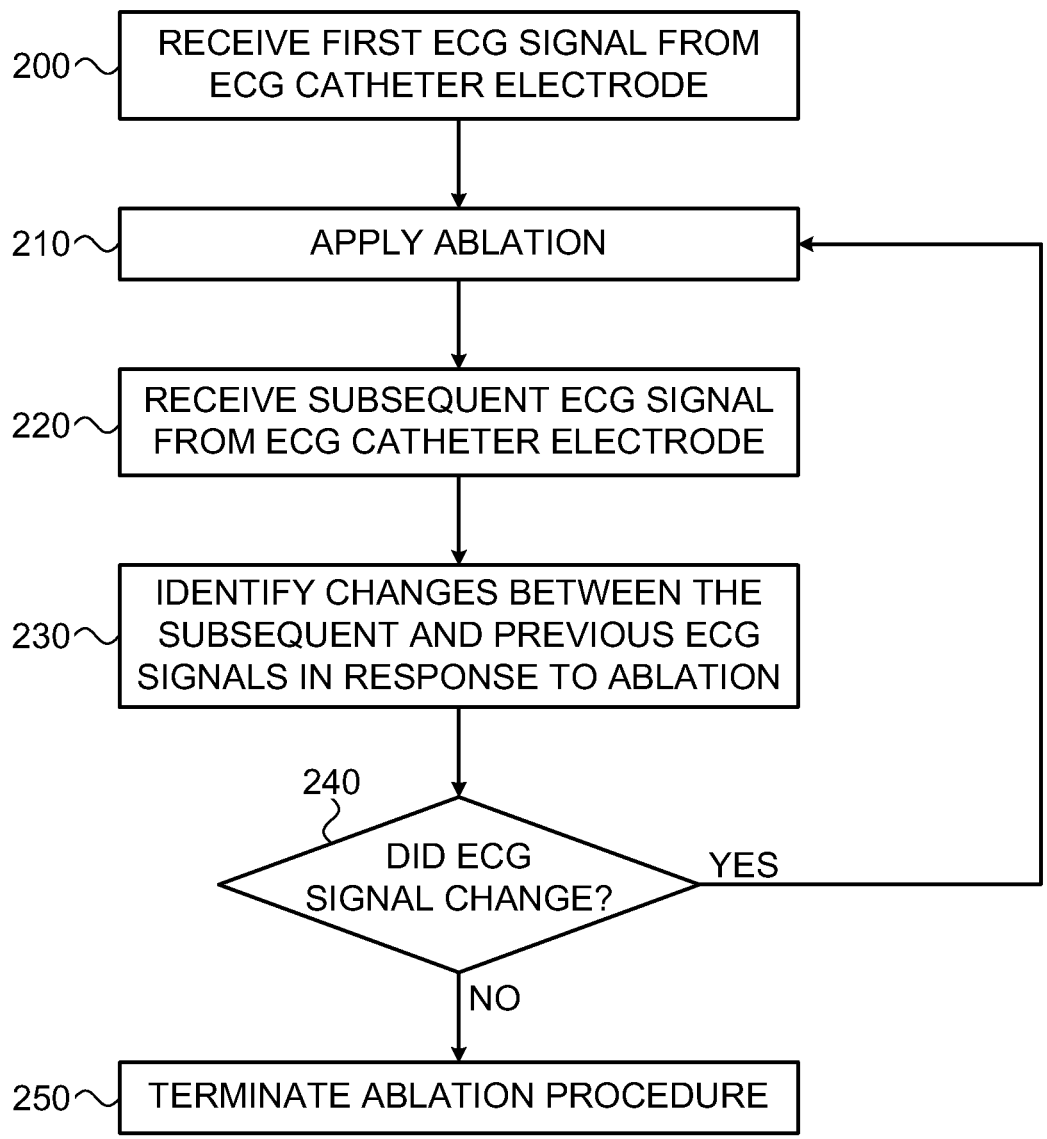
FIG. 3 is a flow chart that schematically illustrates a method for monitoring an electrocardiogram signal after successive ablation cycles, in accordance with an embodiment of the present invention.

FIG. 3 is a flow chart that schematically illustrates a method for monitoring an electrocardiogram signal after successive ablation cycles, in accordance with an embodiment of the present invention. In a first receive step 200, a first ECG signal is received from ECG catheter electrode 40. This data is stored, as a first ECG signal data set, in a storage medium within the processor. In an application step 210, ablation is applied to heart 50 in region 55. In a subsequent receive step 220, a subsequent ECG signal is received from ECG catheter electrode 40. In an identification step 230, processor 25 identifies changes between the subsequent and previously acquired ECG signals in response to ablation, typically after the ablation performed in step 210 has ceased. The processor compares the subsequent ECG signal data set to that of previously acquired ECG data sets to identify changes in the ECG signal due to ablation cycles. From the comparison, the processor may identify one or more time intervals in the ECG waveform where the ECG signal has changed due to the ablation. In a decision step 240, processor 25 assesses if, in step 230, there has been a change in ECG signal levels between the subsequent and previous sets of data. If the assessment is positive, i.e., the ECG signals changed, then the flow chart returns to ablation step 210, so that step 210 and step 220 repeat in an iterative process. If in step 240 there has been no change, the ablation procedure is terminated in a termination step 250, typically so as to prevent heart damage due to over-ablation.

The changes occurring in the ECG signal typically occur in particular time intervals as exemplified by time intervals B and D (FIG. 2). Consideration of the waveforms of FIG. 2 and of the flow chart of FIG. 3 demonstrates that waveform 130 corresponds to a remote-field contribution to the ECG signal and that the differences between waveform 130 and waveforms 100, 110, or 120 correspond to a local component of the signal.

Although the embodiment described in FIG. 2 and FIG. 3 refers to the one or more identified time intervals in which the ECG signal responds to ablation, FIG. 2 and FIG. 3 are merely for conceptual clarity and not by way of limitation whatsoever of the embodiments of the present invention. Any change in the ECG waveform shape in the one or more identified time intervals after successive ablation cycles can be related to the local component of the received ECG signal responding to ablation as described previously.

Although the embodiments described herein typically address the real-time monitoring of ECG signals during cardiac ablation therapy, the methods and systems described herein can also be used in other applications, such as in monitoring neuro-electrical signals during RF ablation therapy of brain tumors.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
an intra-body probe comprising an electrode, which is configured to contact tissue in a heart, wherein the electrode is configured to receive ECG signals and apply a radio frequency ablation signal; and
a processor, which is configured to receive an electrical signal from the electrode, the electrical signal comprising a local component and a remote-field contribution, to distinguish the local component, due to the tissue with which the electrode is in contact, in the electrical signal from the remote-field contribution to the signal, and to control a therapeutic procedure applied to the tissue responsively to the distinguished local component.

2. The apparatus according to claim 1, wherein the therapeutic procedure comprises cardiac ablation therapy.

3. The apparatus according to claim 1, wherein the intra-body probe comprises an additional electrode that is configured to apply an ablation signal to the heart tissue.

4. The apparatus according to claim 1, wherein the electrode applies an ablation signal to the tissue in the heart.

5. The apparatus according to claim 1, wherein the signal comprises a received electrocardiogram (ECG) signal.

6. The apparatus according to claim 1, wherein the local component is in response to cardiac electrical activity generated in the heart within a target ablation region, and the remote-field contribution is in response to cardiac electrical activity generated in the heart outside the target ablation region.

7. The apparatus according to claim 1, wherein the processor is configured to distinguish the local component by identifying one or more time intervals in the received signal in response to a change in the received signal.

8. The apparatus according to claim 7, wherein the processor is configured to distinguish the remote-field contribution by detecting no change in the received signal in one or more additional time intervals outside of the one or more identified time intervals.

9. The apparatus according to claim 7, wherein the processor is configured to initiate a termination of an ablation procedure by detecting that the signal within the one or more identified time intervals no longer changes during to successive ablation cycles.

10. A method, comprising:
receiving an electrical signal from an intra-body probe comprising an electrode configured to contact tissue in a heart, the electrical signal comprising a local component and a remote-field contribution;

distinguishing the local component, due to the tissue with which the electrode is in contact, in the electrical signal from the remote-field contribution to the signal;

configuring the electrode to receive ECG signals and apply a radio frequency ablation signal and controlling a therapeutic procedure applied to the tissue responsively to the distinguished local component, wherein the therapeutic procedure comprises RF ablation.

11. The method according to claim 10, wherein receiving the electrical signal comprises receiving an electrocardiogram (ECG) signal.

12. The method according to claim 10, wherein the local component is in response to cardiac electrical activity within a target ablation region and the remote-field contribution is in response to cardiac electrical activity generated in a region of the heart outside of the target ablation region.

13. The method according to claim 10, wherein distinguishing the local component comprises identifying one or more time intervals in the received signal in response to a change in the received signal.

14. The method according to claim 13, wherein distinguishing the remote-field contribution comprises detecting no change in the received signal in one or more additional time intervals outside of the one or more identified time intervals.

15. The method according to claim 14, wherein controlling the therapeutic procedure comprises initiating a termination of a cardiac ablation procedure in response to detecting that the signal within the identified time intervals no longer changes during to successive ablation cycles.

* * * * *